(12) United States Patent
Bennett et al.

(10) Patent No.: US 8,496,713 B2
(45) Date of Patent: Jul. 30, 2013

(54) SPINE STABILIZATION DEVICE AND METHODS

(75) Inventors: Jeff Bennett, Pottstown, PA (US); Edward Dwyer, Pittsgrove, NJ (US)

(73) Assignee: Globus Medical, Inc., Audubon, PA (US)

( * ) Notice: Subject to any disclaimer, the term of this patent is extended or adjusted under 35 U.S.C. 154(b) by 220 days.

(21) Appl. No.: 12/964,946

(22) Filed: Dec. 10, 2010

(65) Prior Publication Data

US 2012/0150298 A1    Jun. 14, 2012

(51) Int. Cl.
*A61F 2/44*        (2006.01)
(52) U.S. Cl.
USPC .................... 623/23.41; 623/17.11; 623/18.11
(58) Field of Classification Search
USPC .......... 623/17.11, 17.15, 18.11, 19.11, 19.12, 623/20.11–20.15, 20.22, 23.41
See application file for complete search history.

(56) References Cited

U.S. PATENT DOCUMENTS

| | | | |
|---|---|---|---|
| 2005/0033432 A1* | 2/2005 | Gordon et al. | 623/17.11 |
| 2009/0043391 A1* | 2/2009 | de Villiers et al. | 623/17.16 |
| 2009/0088850 A1* | 4/2009 | Froehlich | 623/17.16 |

* cited by examiner

*Primary Examiner* — Kevin T Truong
*Assistant Examiner* — Christian Sevilla

(57) ABSTRACT

An implant stabilizes two adjacent bones of a joint, while enabling a natural kinematic relative movement of the bones. Support components are connected to each bone of the joint, and a flexible core is interposed between them. The core and at least one of the support components are provided with a smooth sliding surface upon which the core and support component may slide relative to each other, enabling a corresponding movement of the bones. The surfaces may have a mating curvature, to mimic a natural movement of the joint. The core is resilient, and may bend or compress, enabling the bones to move towards each other, and or to bend relative to each other.

17 Claims, 4 Drawing Sheets

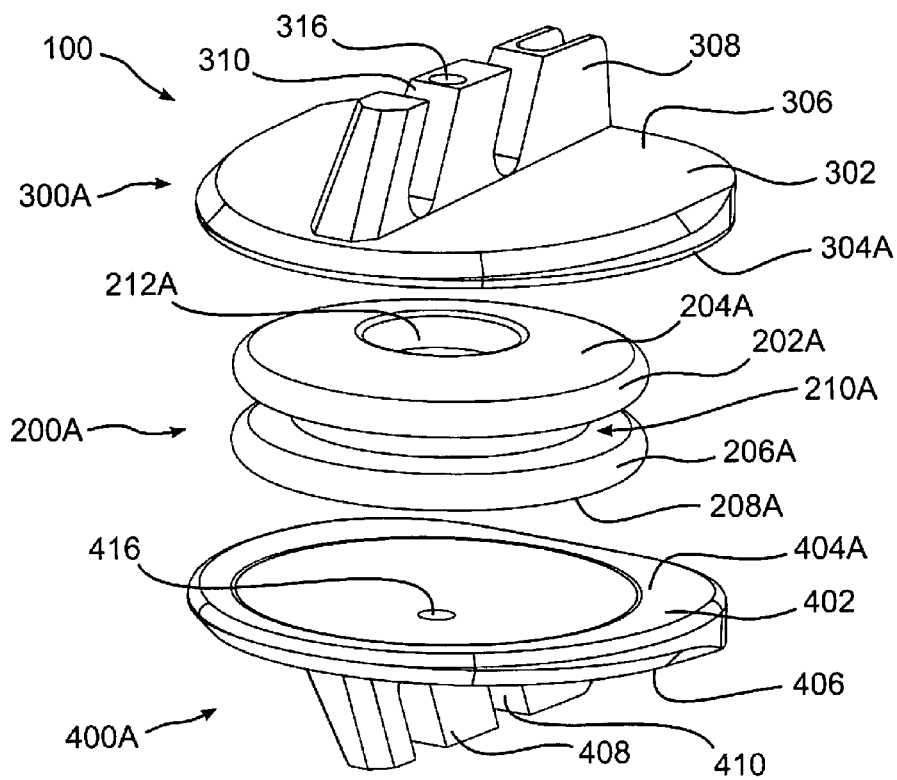
Fig. 5
Fig. 6
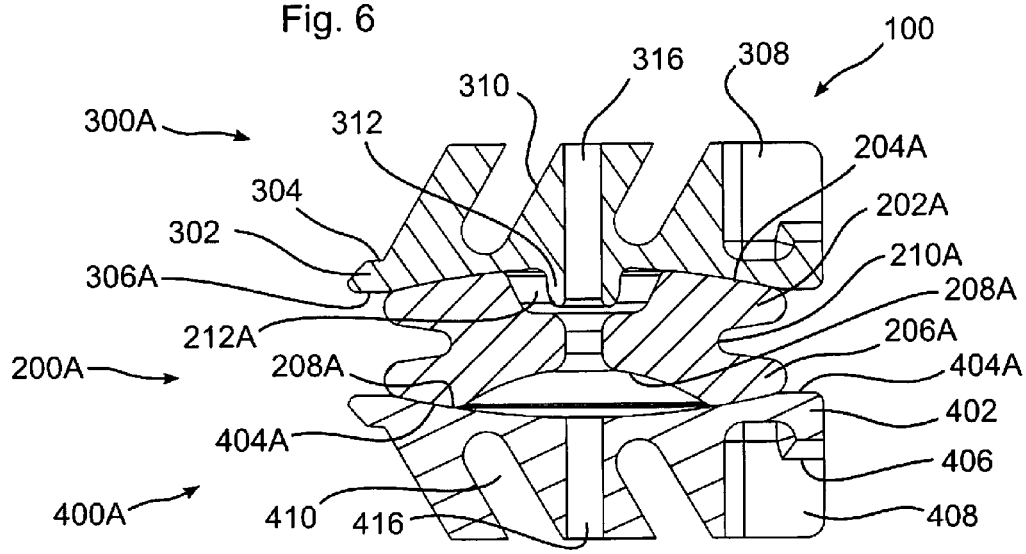

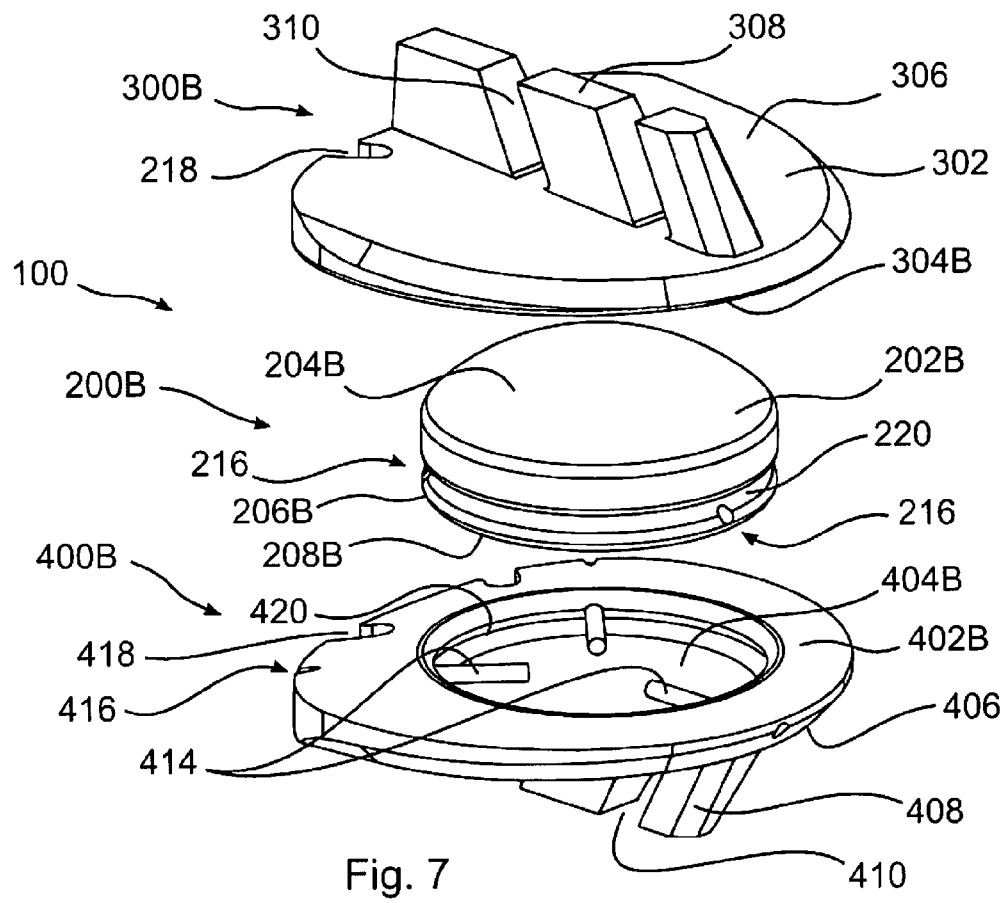
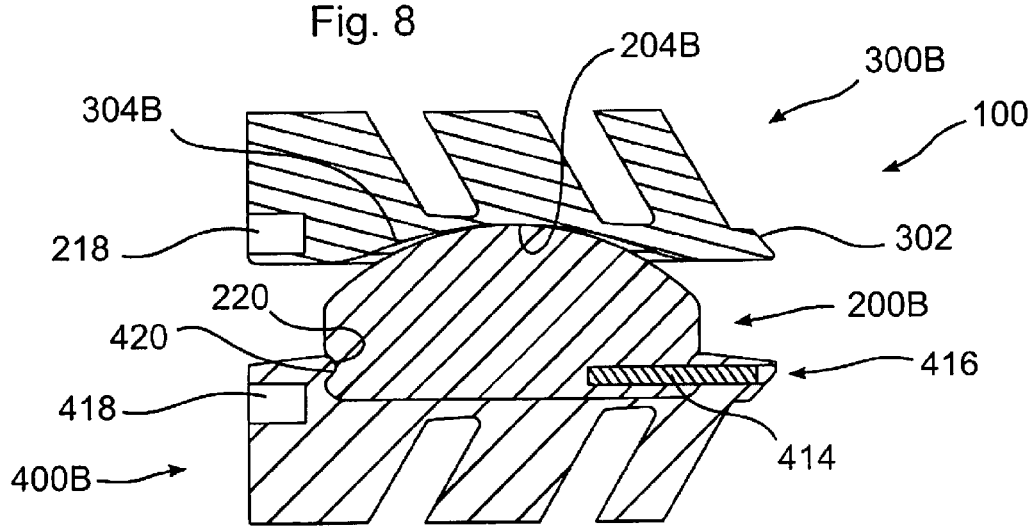

SPINE STABILIZATION DEVICE AND METHODS

FIELD OF THE INVENTION

This invention relates to stabilizing adjacent vertebrae of the spine, after surgery or trauma, while preserving a natural kinematic signature.

BACKGROUND OF THE INVENTION

Intervertebral devices are used to address diseases or disorders of the spine, or to address damage due to trauma. These devices operate, for example, to stabilize, guide, or limit movement of adjacent vertebrae, while bearing weight. There is a need for a spinal disc assembly that mimics the motion and characteristics of the natural spinal disc. In particular, there is a need for a spinal disc which mimics the six degrees of motion associated with the natural spinal disc.

SUMMARY OF THE INVENTION

An implant in accordance with the invention includes a flexible core, a first support component, operative to contact a first engaging surface of the core, and a second support component, operative to contact a second, opposing engaging surface of the core.

The implant of the invention is operative, when positioned between adjacent bones of a joint, such as adjacent vertebrae, to stabilize the joint. The implant further enables a natural kinematic movement of the joint, while limiting movement beyond a therapeutic range of motion.

A flexible core is provided with an inflection region of greater flexibility, which enables a displacement or changed orientation of opposed engaging surfaces of the core. In one embodiment, the core tapers at one end to form the inflection region, and which may deform or buckle to enable a relative angular displacement of engaging surfaces.

In addition, the core may compress to reduce a distance between portions of first and second engaging surfaces. Compression may include an expansion of material outwards relative to an interior of the core, or material of the core may collapse into an interior.

A tether, or lanyard may be provided, operative to limit a maximum displacement of the core and one or both of the first and second support components. The lanyard is affixed to two of either core and one or both support components. The lanyard is formed of a flexible material which does not prevent movement within an intended range of motion of the implant, and may advantageously be formed of a resilient material, to avoid an abrupt relative cessation of movement at a limit of travel.

Each support component includes an engagement plate having a core engaging surface and a bone engaging surface. A keel or other projection extends from the bone engaging surface, and is operative to engage a bony surface, for example, an interior portion of a vertebra. The projection may include a bone ingrowth surface, region, or spaces, to further secure the plate into engagement with the bone. Core engaging surfaces of the first and second support component are advantageously formed with a lubricious material relative to a surface material of the engaging surfaces of the core, if sliding or rotating relative to the core is intended.

In one embodiment, an inflection region of the core is most flexible at a point proximate an engaging surface. A hollow interior may be included, operative to provide a space into which material forming the inflection region may deflect. A core engaging surface is provided with a smooth surface, upon which a second engaging surface of the flexible core may slide.

Relative motion of bones, for example opposing bones of a joint, result from movement of a patient into which an implant of the invention is implanted. As the first and second support components are attached to these bones, a corresponding motion is induced in the support components. In the natural body of the patient, these bones move in accordance with six degrees of motion. Each of these degrees of motion are enabled with an implanted implant of the invention, as follows, with reference to FIG. 4:

(1) translation in the direction indicated by line "X", corresponding to the core sliding along an engaging surface;

(2) translation in the direction indicated by line "Y", corresponding to axial compression of the core;

(3) translation in the direction indicated by line "Z", corresponding to the core sliding along an engaging surface;

(4) rotation about an axis indicated by line "X", corresponding to compression of one side of the core;

(5) rotation about an axis indicated by line "Y", corresponding to the corerotating upon an engaging surface; and (6) rotation about an axis indicated by line "Z", corresponding to compression of one side of the core.

Alternatively stated, if an axis of the implant is defined as extending through an implant of the invention from a first adjacent bone to a second adjacent bone, the implant would enable relative motion of the first and second adjacent bones with respect to:

(a) opposite rotation about the axis;
(b) axially bending;
(c) axially compressing; and
(d) radial sliding with respect to the axis.

In an alternative embodiment, the core includes first and second segments separated by an inflection region that is substantially narrower than flanking segments, and thus bends to enable an angular displacement of the segments and their associated engaging surfaces.

In one embodiment of the invention, at least a portion of the support component has a core engaging surface configured as a curved smooth surface which slidably engages a mating region of the core. A curved slidable portion of the core engaging surface is recessed within a support component, and a mating slidable portion of an engaging surface projects from the core; alternatively, the core engaging surface may be projected, and an engaging surface of the core may be recessed.

Similarly, both sides of the core may be curved, each side mateable with a curved surface of a support component, for example, forming two convex surfaces. Mating surfaces on both sides of the core, for example, operate to foster a desired kinematic movement, and maintain a desired ligament tension throughout the expected range of motion. It should be understood, however, that in accordance with the invention, either surface may be either convex, concave, or flat, as the therapeutic needs of the patient dictate. In use, a configuration with a curved mating surface enables all six degrees of movement as described above, however, due to the mating curved slidable engaging surfaces, additional directional stability is provided.

In a further embodiment, the core is provided with a flat surface at a second engaging surface, which is matably connectable to a flat core engaging surface of a support component. One or more pins pass through pin bores or apertures provided in the core and support component, locking the two components together. In addition, a snap fit engagement between recessed and projecting portions of the core and a support component may be provided to further secure the core and support component together.

In yet another embodiment of the invention, the core engaging surface has a curved portion having a radius which is larger than a curved portion of a mating portion of the core. As such, the core may slide relative to the support component. The core may at the same time be rotated, and compressed evenly or laterally.

Mating surfaces of the core and a support component may include concave, convex, semi-spherical, or barrel shapes, whereby a resistance to sliding, spinning, rotating, rocking, or other relative movement may be uniform in all directions, or different in specific directions.

The invention provides a joint replacement implant, for example for replacement or stabilization of a cervical disc replacement, although other joints may be partially or completely replaced by the implant, for example one or more joints of the fingers, hand, wrist, elbow, shoulder, other areas of the spine, hip, knee, ankle, foot, or toes.

Implants of the invention are operative to restore the natural kinematic signature and natural joint properties, particularly for spinal discs, but for all joints which exhibit movement in all six degrees of motion, as detailed above.

All elements of implant may be made from a flexible material, although the core, in particular, flexes in order to accommodate an angular displacement of first and second support components. As the joint is flexed or extended, the flexible and or resilient material of the core may bulge or stretch to enable an angular displacement of opposing engaging surfaces. Additionally, or alternatively, an inflection region provides a relatively weaker region of the core, which is adapted through thickness and or shape to facilitate bending of the core.

Implant may be fabricated using any biocompatible and materials known to one skilled in the art, having sufficient strength, flexibility, resiliency, and durability for the patient, and for the term during which the device is to be implanted.

In accordance with the invention, a single implant may be used, to provide stabilization for a weakened joint or joint portion. Alternatively, two, three, or more implants may be used, at a single joint level, or in multiple joints. Moreover, implants of the invention may be combined with other stabilizing means.

Any surface or component of the invention may be coated with or impregnated with therapeutic agents, including bone growth, healing, antimicrobial, or drug materials, which may be released at a therapeutic rate, using methods known to those skilled in the art.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 5 depicts a perspective exploded view of another embodiment of an implant of the invention;

FIG. 6 illustrates a cross section of the implant of FIG. 5, taken centrally through bone engaging projections of the implant;

FIG. 7 depicts a perspective exploded view of a further embodiment of an implant of the invention; and, FIG. 8 illustrates a cross section of the implant of FIG. 7, taken centrally through bone engaging projections of the implant;

DETAILED DESCRIPTION OF THE INVENTION

In the description which follows, any reference to direction or orientation is intended primarily and solely for purposes of illustration and is not intended in any way as a limitation to the scope of the present invention. Also, the particular embodiments described herein are not to be considered as limiting of the present invention.

Figure 1:
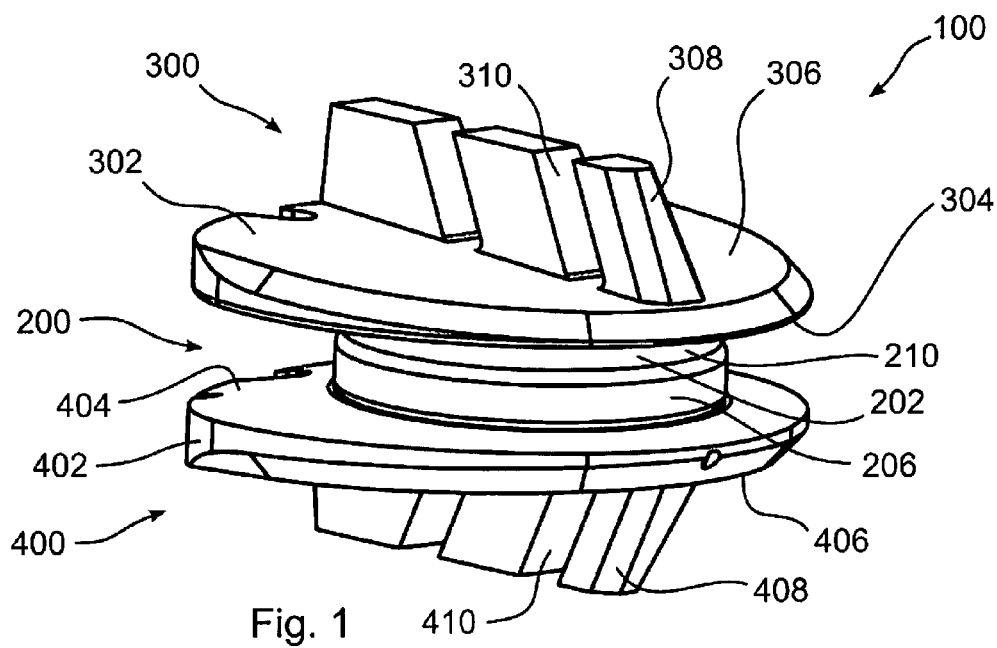
FIG. 1 depicts a perspective view of an implant in accordance with the invention.
Figure 2:
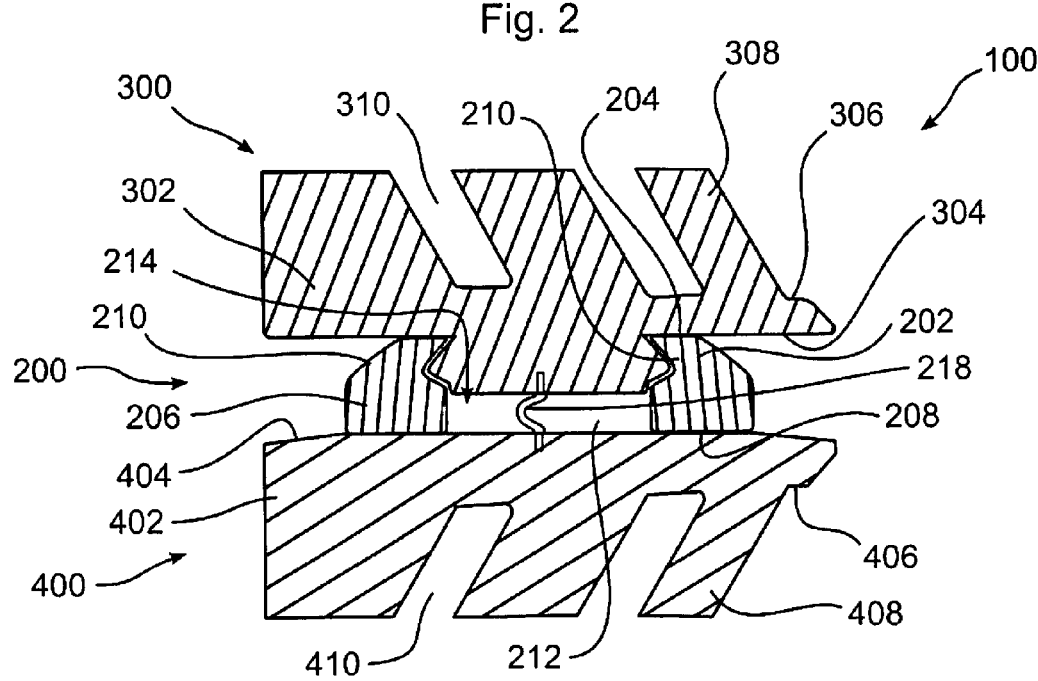
FIG. 2 illustrates a cross section of the implant of FIG. 1, taken centrally through bone engaging projections of the implant.

Referring now to the figures, in which like reference numerals refer to like elements, FIGS. 1 and 2 illustrate an implant 100 in accordance with the invention, including a flexible core 200, a first support component 300, operative to contact a first engaging surface 204 of core 200, and a second support component 400, operative to contact an opposing second engaging surface 208 of core 200.

Figure 3:
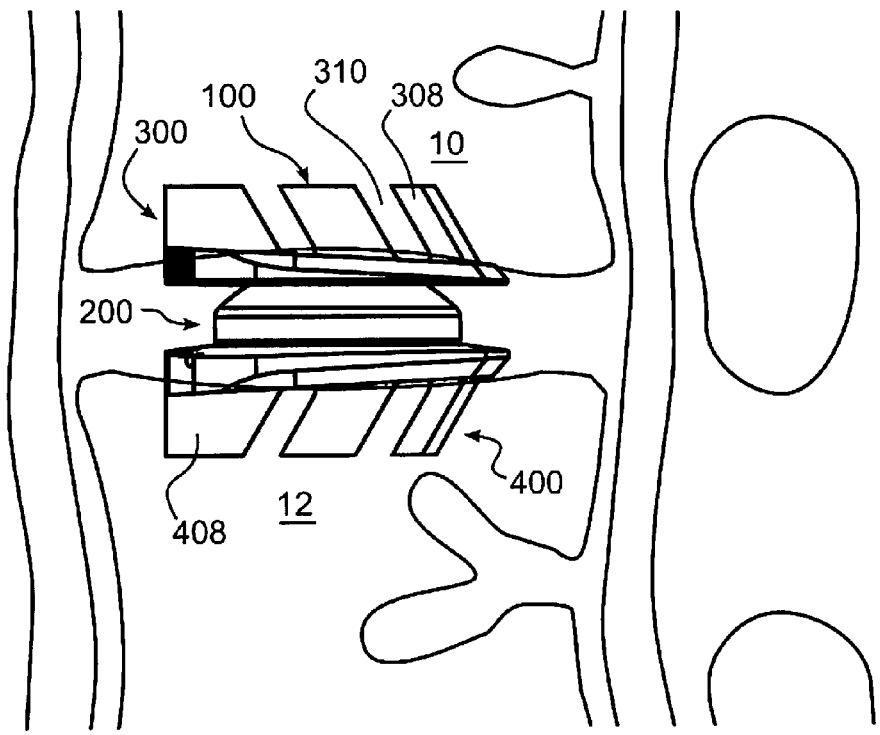
FIG. 3 illustrates the implant of FIG. 1, positioned between two adjacent bones in a body.

With reference to FIG. 3, implant 100 is operative, when positioned between adjacent bones of a joint, such as for example vertebrae 10, 12, to stabilize a joint formed by adjacent vertebrae. Implant 100 further enables natural kinematic movement of the joint while limiting movement beyond a therapeutic range of motion. In one embodiment, this range of motion reflects the complete natural kinematic signature for the patient.

Referring again to FIGS. 1 and 2, flexible core 200 includes a first engaging surface 204 disposed upon a first segment 202, and a second engaging surface 208, disposed upon a second segment 206. In the embodiment shown in FIGS. 1 and 2, flexible core 200 is provided with an inflection region 210 of greater flexibility, which enables a displacement or changed orientation of engaging surface 204 with respect to engaging surface 208. In particular, first segment 202 tapers at one end to form inflection region 210, which may deform or buckle to enable a relative angular displacement of engaging surfaces 204, 208.

In addition, core 200 may compress to reduce a distance between portions of first and second engaging surfaces 204, 208. Compression may include an expansion of material outwards relative to an interior 214 of core 200, resulting in an increase in a diameter of core 200, or material of core 200 may collapse into an interior of core 200, thereby partially or completely maintaining an exterior dimension of core 200. Alternatively, spaces within the material of core 200 may be reduced in size, for example spaces formed by a cellular or porous matrix of the material of core 200 may compress, whereby expansion of an exterior dimension of core 200 may be maintained or limited.

First support component 300 includes an engagement plate 302 having a core engaging surface 304, and a bone engaging surface 306. A keel or other projection 308 extends from bone engaging surface 306, and is operative to engage a bony surface, for example, an interior portion of vertebra 10 or 12. Projection 308 includes bone ingrowth spaces 310, operative to provide an area for bone ingrowth, to further secure plate 302 into engagement with the bone to which plate 302 is attached.

Second support component 400 includes an engagement plate 402 having a core engaging surface 404, and a bone engaging surface 406. A keel, extension, or projection 408 extends from bone engaging surface 406, and is operative to engage a bony surface, for example, an interior portion of vertebra 10 or 12. Projection 408 includes bone ingrowth spaces 410, operative to provide an area for bone ingrowth, to further secure plate 402 into engagement with the bone to which plate 402 is attached.

Bone ingrowth spaces 310, 410 may each advantageously be formed at an angle with respect to a direction of projection 308, 408 insertion, thereby potentially reducing an incidence of separation of implant 100 from the bone, after bone ingrowth has taken place.

Core engaging surfaces 304, 404 of first and second support component 300, 400 are advantageously formed with a lubricious material relative to a surface material of engaging surface 204, 208 of core 200, if sliding or rotating relative to core 200 is intended.

FIG. 2 additionally illustrates a tether, or lanyard 218, operative to limit a maximum displacement of core 200 and one or both of first and second support components 300, 400. Lanyard 218 is affixed to two of either core 200 and one of support components 300, 400, or both support components 300, 400. Lanyard 218 is formed of a flexible material which does not prevent movement within an intended range of motion of implant 100, as described herein, and may advantageously be formed of a resilient material, to avoid an abrupt relative cessation of movement, at a limit of travel, of elements to which it is affixed.

In the embodiment of FIGS. 1-4, inflection region 210 is most flexible at a point proximate engaging surface 204. A hollow interior 212 may be included, operative to provide a space into which material forming region 210 may deflect during displacement of engaging surface 204 relative to engaging surface 208. A tether 218 may be provided, operative to limit a maximum extent of motion of first and second support components 300, 400. In this embodiment, core engaging surface 404 is provided with a smooth surface, upon which a second engaging surface of flexible core 200 may slide. Core engaging surface 404 is illustrated as substantially planar in FIG. 4, although a projection and recess, as described for FIGS. 1 and 2, may alternatively be provided. A lip or raised portion extending from core engaging surface 404, not shown, may further, or in alternative to lanyard 218, operate to limit an extent of movement of engaging surface 208 upon core engaging surface 404.

Figure 4:
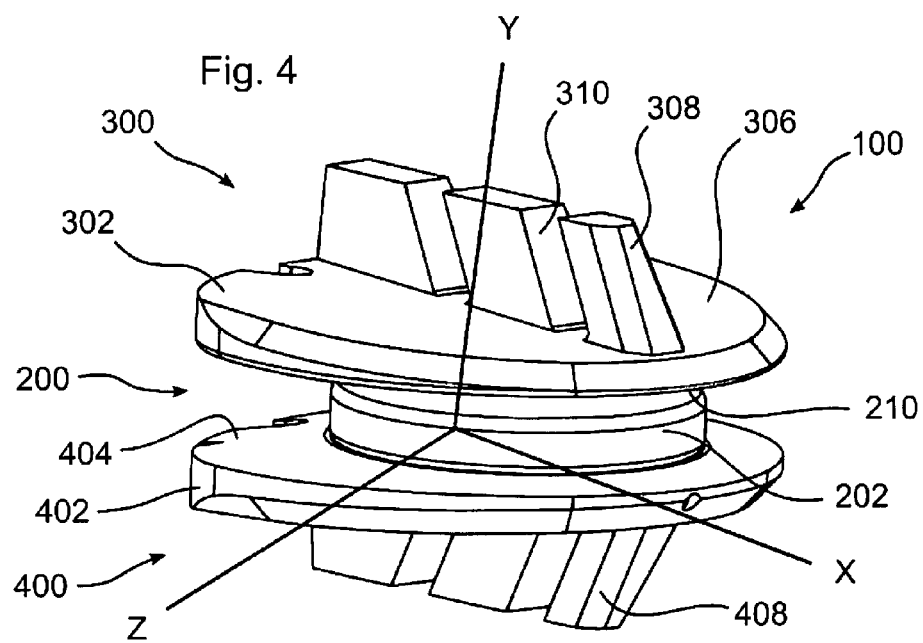
FIG. 4 illustrates the implant of FIG. 1, with lines indicating degrees of motion of the implant.

With reference to FIGS. 3 and 4, relative motion of bones 10 and 12 result from movement of a patient into which implant 100 is implanted. As first and second support components 300, 400 are attached to bones 10, 12, respectively, a corresponding motion is induced in components 300, 400. It should be understood that, in accordance with the invention, component 400 may be connected to bone 10, and component 300 may be connected to bone 12; that is, either component 300 or 400 may be positioned superiorly with respect to the other.

In the natural body of the patient, bones 10 and 12 move in accordance with six degrees of motion. Each of these degrees of motion is enabled with an implanted implant 100, as diagrammed in FIG. 4. Specifically:

(1) translation in the direction indicated by line "X", corresponding to core 200 sliding along engaging surface 404;

(2) translation in the direction indicated by line "Y", corresponding to axial compression of core 200;

(3) translation in the direction indicated by line "Z", corresponding to core 200 sliding along engaging surface 404;

(4) rotation about an axis indicated by line "X", corresponding to compression of one side of core 200;

(5) rotation about an axis indicated by line "Y", corresponding to core 200 rotating upon engaging surface 404; and (6) rotation about an axis indicated by line "Z", corresponding to compression of one side of core 200.

Alternatively stated, if an axis of the implant is defined as extending through an implant of the invention from a first adjacent bone to a second adjacent bone, the implant would enable relative motion of the first and second adjacent bones with respect to:

(a) opposite rotation about the axis;
(b) axially bending;
(c) axially compressing; and
(d) radial sliding with respect to the axis.

In an alternative embodiment, shown in FIGS. 5 and 6, core 200A includes first and second segments 202A, 206A, separated by an inflection region 210A that is substantially narrower than flanking segments 202A, 206A, and thus bends to enable an angular displacement of segments 202A, 206A, and accordingly enables an angular relative displacement of engaging surfaces 204A, 208A.

FIG. 6 illustrates a cross-section of the implant 100 of FIG. 5, taken through projections 308 and 408. At least a portion of core engaging surface 404A is configured as a curved smooth surface upon which a mating region of curved smooth surface of second engaging surface 208A of flexible core 200A may slide. In the illustration, a curved slidable portion of core engaging surface 404A is recessed within second support component 400A, and a mating slidable portion of engaging surface 208A projects from core 200A; however, it should be understood that engaging surface 404A may be projected, and engaging surface 208A may be recessed.

Similarly, a portion of first engaging surface 204A is a curved smooth surface upon which a mating curved smooth surface of core engaging surface 306A may slide. In the embodiment shown in FIGS. 5-6, core 200A forms two convex surfaces 204A, 208A, to foster a desired kinematic movement, and to maintain a desired ligament tension throughout the expected range of motion, and to promote a natural resting position of the bones. It should be understood, however, that in accordance with the invention, either surface 204A or 208A may be either convex or concave, as the therapeutic needs of the patient dictate. Alternatively, either surface may be flat, as illustrated in FIGS. 1-4, discussed above, or FIGS. 7-8, discussed below.

In one embodiment, a projection 312 extends from first engaging surface 306A into core aperture or hollow interior 212A, and is operative to limit an extent of movement of first support component 300 with respect to core 200. A similar configuration could be provided for slidably mating engaging surfaces 404A and 208A.

Embodiments of the invention may be provided with one or more apertures 316, 416 through which fasteners may be installed, to further secure implant 100 within a patient. For example, a bone screw may be passed through aperture 316 in first support component 300 and into bone 10, and another bone screw may be passed through aperture 416 in second support component 400, and into bone 12. A bone growth agent may alternatively or additionally be provided within aperture 316 or 416, or upon bone engaging surface 306 and or 406, to promote bone growth thereinto. Bone growth surfaces may be provided with openings or texture into which tissue may grow and adhere.

In use, the embodiment of FIGS. 5-6 enables all six degrees of movement as described above, however, due to the mating curved slidable engaging surfaces 208A and 404A, additional directional stability is provided, whereby sliding is inhibited to an extent in the absence of flexion or extension of the joint.

This inhibition arises from a natural gravitational resting state of the mating curved engaging surfaces 208A and 404A.

Referring now to the embodiment illustrated in FIGS. 7-8, in which core 200B is provided with a flat surface at second engaging surface 208B, matably connectable to flat core engaging surface 404B of second support component 400. In this embodiment, core 200B is configured to affix core 200B with respect to rotation upon second engaging surface 404B, by one or more pins 414, which pass through one or more pin bores or apertures 216, 416, provided in core 200B and second support component 400B, respectively. While pins are illustrated, it should be understood that other fastener configuration are possible, including screws, adhesive, set screws, interference fit, press fit, or other methods as would be understood by one skilled in the art. Pins 414 may be threaded or press fit into apertures 216 or 416, or secured using adhesive, and may be secured to either or both of core 200B or second support component 400B.

While pins 414 may be utilized to prevent rotation as well as to maintain core 200B in a position upon engagement surface 404B, an axial position of core 200B against engagement surface 404B may alternatively or additionally be maintained by a snap fit engagement between recessed portion 220 and projected portion 420 of core 200B and core engaging surface 404B, respectively. Alternatively, core 200B may be provided with a projecting portion, and core engaging surface 404B may be provided with a mating recess.

In any of the embodiments of the invention, should it be desired to maintain a position of either or both core engagement surfaces 304, 304A, 304B and 404, 404A, 404B relative to core 200, 200A, 200B, pins, a snap fit, or other fasteners may be used, as described above.

With further reference to FIG. 8, it can be seen that core engaging surface 304B has a curved portion having a radius which is larger than a curved portion of first engaging surface 204B. As such, core engaging surface 304B and first engaging surface 204B may readily slide, to a limited extent, relative to each other, as influenced by the difference between their respective curvatures. Core 200B may also be rotated, and compressed evenly or laterally, as detailed elsewhere herein with respect to other embodiments.

It should be understood that superior and inferior positions of components, as illustrated, are for the convenience of the reader in understanding the invention, and that implant 100 may be implanted in a reverse orientation than is shown, as benefits the patient.

In use, the embodiment of FIGS. 7-8 enables all six degrees of movement as described above, however, due to the mating curved slidable engaging surfaces 204B and 304B, additional directional stability is provided, whereby sliding is inhibited to an extent in the absence of flexion or extension of the joint. This inhibition arises from a natural gravitational resting state of the mating curved engaging surfaces 204B and 304B. Rotation, or spinning, of bone 10 with respect to bone 12, is translated only through an interface between first engaging surface 204B and core engaging surface 304B, as second engaging surface 208B is affixed with respect to core engaging surface 404B. Similarly, sliding is carried out solely through this interface, for the same reasons. Surfaces 208B and 404B may alternatively slide with respect to each other, as detailed herein with respect to other embodiments.

Mating surfaces 204, 204A, 204B and 304, 304A, 304B; or 208, 208A, 208B and 404, 404A, 404B, may, for example, be concave, convex, semi-spherical, elliptical, complex, or barrel shaped, whereby a resistance to sliding, spinning, rotating, rocking, or other relative movement may be uniform in all directions, or different in specific directions.

FIG. 8 further illustrates insertion tool channels, bores, openings, or apertures 218, 418, in first and second support components 300B, 400B. As implant 100 is inserted between joint surfaces maintained in spaced relation by ligaments, it may be necessary to mechanically compress implant 100 prior to insertion within the joint. A tool, not shown, such as is known in the art, may be provided with tines which engage tool apertures 218, 418, whereupon first and second support components 300B, 400B may be moved together, or apart, as determined by the practitioner, during implantation. Further, implant 100 may be implanted through an anterior, anterolateral, or lateral approach, and accordingly, tool apertures 218, 418 provide a means for mechanically grasping and manipulating implant 100 during implantation.

The invention provides a joint replacement implant, for example for replacement or stabilization of a cervical disc replacement, although other joints may be partially or completely replaced by implant 100, for example one or more joints of the fingers, hand, wrist, elbow, shoulder, other areas of the spine, hip, knee, ankle, foot, or toes.

Implant 100 is operative to restore the natural kinematic signature and natural joint properties, particularly for spinal discs, but for all joints which exhibit movement in all six degrees of motion, as detailed above.

All elements of implant 100 may be made from a flexible material, although core 200, in particular, flexes in order to accommodate an angular displacement of first and second support components 300, 400. As the joint is flexed or extended, the flexible and or resilient material of core 200 may bulge or stretch to enable an angular displacement of first and second engaging surfaces 204, 208. Additionally, or alternatively, inflection region 210 provides a relatively weaker region of core 200 which is adapted through thickness and or shape to facilitate bending of core 200.

Implant 100 may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics.

Portions or all of the implant may be radiopaque or radiolucent, or materials having such properties may be added or incorporated into the implant to improve imaging of the device during and after implantation.

Opposing mating surfaces which rotate, spin, or slide, including core engaging surfaces 304, 304A, 304B, 404, 404A, 404B, and first and second engaging surfaces 204, 204A, 204B and 208, 208A, 208B, may be made of the same or different materials, which combination produces a therapeutic fluidity of motion, or desired drag. Surfaces of implant 100 may be plasma sprayed, for example by titanium plasma spray, and may be bead blasted or electropolished.

More particularly, The support components may be manufactured from cobalt-chrome-molybdenum alloy, Co—Cr—Mo, as specified in ASTM F1537 (and ISO 5832-12). The smooth surfaces may be plasma sprayed with commercially pure titanium, as specified in ASTM F1580, F1978, F1147 and C-633 (and ISO 5832-2). The core may be manufactured from ultra-high molecular weight polyethylene, UHMWPE, as specified in ASTM F648 (and ISO 5834-2).

Core 200, 200A, 200B, may alternatively, in one embodiment, be fabricated using polycarbonate urethane (PCU), or a thermoplastic polycarbonate urethane (TPU) such as Bionate, a registered trademark of DSM IP Assets B.V. Corporation, of Heerlen Netherlands, for a thermoplastic elastomer formed as the reaction product of a hydroxyl terminated polycarbonate, an aromatic diisocyanate, and a low molecular weight glycol used as a chain extender. Other polymeric materials with suitable flexibility, durability, and biocompatibility may also be used, as understood by one skilled in the art.

In accordance with the invention, implants of various sizes may be provided to best fit the anatomy of the patient. Support components and a core of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example angular mating dispositions of support components and core, to provide for a natural lordosis, or a corrective lordosis, for example of from 0° to 6° for a cervical application, although much different values may be advantageous for other joints. Implant heights, for use in the cervical vertebrae for example, may typically range from 5 mm to 9 mm, although the size is dependent on the patient, and the joint into which an implant of the invention is to be implanted.

In accordance with the invention, a single implant 100 may be used, to provide stabilization for a weakened joint or joint portion. Alternatively, two, three, or more implants 100 may be used in multiple joints. Moreover, implants 100 may be combined with other stabilizing means.

Additionally, implant 100 may be fabricated using material that biodegrades in the body during a therapeutically advantageous time interval. Further, implant 100 is advantageously provided with smooth and or rounded exterior surfaces, which reduce a potential for deleterious mechanical effects on neighboring tissues.

Any surface or component of the invention may be coated with or impregnated with therapeutic agents, including bone growth, healing, antimicrobial, or drug materials, which may be released at a therapeutic rate, using methods known to those skilled in the art.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An implant for stabilizing first and second adjacent bones in a patient, comprising:
    a first support component having a first side adapted to be affixed to the first bone of the patient, and a second side opposite the first side having a smooth surface;
    a resilient core having a third side having a smooth surface and positionable in mating slidable engagement with the second side, said resilient core further including a fourth side opposite the third side;
    a second support component having a fifth side mateable with the fourth side, and a sixth side opposite fifth side adapted to be affixed to the second bone of the patient;
    whereby an axis of the implant is defined as extending through said implant from the first adjacent bone to the second adjacent bone;
    wherein said core is positionable between said first and second support components to thereby be positionable between the first and second adjacent bones; and
    wherein said core separates at least a portion of each of said first and second supports at a relative first distance along said axis, said core being resiliently deformable under pressure to separate said at least a portion each of said first and second supports at a second, lesser relative distance along said axis; and wherein said core may slide upon said third side, in engagement with said second side, in a radial direction with respect to said axis; and
    wherein when said first support component is affixed to the first adjacent bone, and said second support component is affixed to the second adjacent bone, and said core is positioned between said first and second support components, the first and second adjacent bones are stabilized, and said core may both resiliently deform and slide separately or simultaneously, to enable a kinematic movement of the two adjacent bones similar to a natural kinematic movement of the bones
    whereby the fifth side of the second support component that is mateable with the fourth side of the resilient core has a curved portion having a radius that is different from a radius of the curved portion of the second support component; wherein a pin member extends through the first support component and the resilient core to attach the first support component to the resilient core.

2. The implant of claim 1, wherein said core includes a polymeric material.

3. The implant of claim 1, wherein the fourth and fifth sides are provided with smooth surfaces slidable in engagement with each other.

4. The implant of claim 1, wherein one of said smooth surfaces of the second side and third side have a convex shape, and the other has a mating concave shape.

5. The implant of claim 3, wherein one of said smooth surfaces of the fourth and fifth sides have a convex shape, and the other has a mating concave shape.

6. The implant of claim 1, wherein said resilient core includes a region adapted to bend, whereby when said core is positioned between said first and second support components and said region is bent, an angle defined by second and fifth sides is changed.

7. The implant of claim 6, wherein said region adapted to bend defines a periphery of said core having a reduced diameter.

8. The implant of claim 7, wherein said periphery is a central ring, bounded by upper and lower rings of larger diameter relative to said central ring, said central ring operative to inflect, enabling a bending of said core.

9. The implant of claim 1, further including a projection associated with said first or sixth side, operative to be inserted into the first or second adjacent bone, to improve a connection of first or sixth side with the first or second adjacent bone.

10. The implant of claim 9, wherein said projection includes at least one space, operative to provide a space for bone ingrowth.

11. The implant of claim 10, wherein said space extends from an open end of said projection in a direction of said first side, extending at an angle with respect to said axis.

12. The implant of claim 1, further including at least one opening operative to admit a tool part useful for inserting said implant into a space between the adjacent bones.

13. The implant of claim 1, wherein the adjacent bones are located among the lumbar vertebrae.

14. The implant of claim 1, wherein the adjacent bone are located among the cervical and thoracic vertebrae.

15. The implant of claim 1, wherein the implant enables relative motion of the first and second adjacent bones with respect to: (a) opposite rotation about the axis; (b) axially bending; (c) axially compressing; and (d) radial sliding with respect to the axis.

16. An implant for stabilizing first and second adjacent bones in a patient, comprising:
  a first support component having a first side adapted to be affixed to the first bone of the patient, and a second side opposite the first side having a smooth surface;
  a resilient core having a third side having a smooth surface and positionable in mating slidable engagement with the second side, said resilient core further including a fourth side opposite the third side, said core further including an inflected region operative to facilitate bending of said core, wherein the third side of the resilient core is flat and the fourth side opposing the third side of the resilient core is curved;
  a second support component having a fifth side mateable with the fourth side, and a sixth side opposite the fifth side adapted to be affixed to the second bone of the patient;
  whereby an axis of the implant is defined as extending through said implant from the first adjacent bone to the second adjacent bone;
  wherein said core is positionable between said first and second support components to thereby be positionable between the first and second adjacent bones; and
  wherein said core separates at least a portion of each of said first and second supports at a relative first distance along said axis, said core being resiliently deformable under pressure to separate said at least a portion each of said first and second supports at a second, lesser relative distance along said axis; and
  wherein said core may slide upon said third side, in engagement with said second side, in a radial direction with respect to said axis; and
  wherein said first support component is rotatable about said axis relative to said second support component;
  wherein when said first support component is affixed to the first adjacent bone, and said second support component is affixed to the second adjacent bone, and said core is positioned between said first and second support components, the first and second adjacent bones are stabilized, and said core may both resiliently deform, rotate, and slide separately or simultaneously, to enable a kinematic movement of the two adjacent bones similar to a natural kinematic movement of the bones; wherein a pin member extends through the first support component and the resilient core to attach the first support component to the resilient core.

17. An implant for stabilizing first and second adjacent bones in a patient, comprising:
  a first support component having a first side adapted to be affixed to the first bone of the patient, and a second side opposite the first side having a smooth concave or convex surface;
  a resilient core having a third side having a smooth concave surface if said second side has a convex surface, or a smooth convex surface if said second side has a concave surface, said third side thereby positionable in mating slidable engagement with the second side, said resilient core further including a fourth side opposite the third side, wherein the resilient core is affixed to the first support component via one or more pins that extend through the first support component and the resilient core to attach the first support component to the resilient core;
  a second support component having a fifth side mateable with the fourth side, and a sixth side opposite the fifth side adapted to be affixed to the second bone of the patient;
  whereby an axis of the implant is defined as extending through said implant from the first adjacent bone to the second adjacent bone;
  wherein said core is positionable between said first and second support components to thereby be positionable between the first and second adjacent bones; and
  wherein said core separates at least a portion of each of said first and second supports at a relative first distance along said axis, said core being resiliently deformable under pressure to separate said at least a portion each of said first and second supports at a second, lesser relative distance along said axis; and
  wherein said core may slide upon said third side, in engagement with said second side, in a radial direction with respect to said axis; and wherein said first support component is rotatable about said axis relative to said second support component;
  wherein when said first support component is affixed to the first adjacent bone, and said second support component is affixed to the second adjacent bone, and said core is positioned between said first and second support components, the first and second adjacent bones are stabilized, and said core may both resiliently deform, rotate, and slide separately or simultaneously, to enable a kinematic movement of the two adjacent bones similar to a natural kinematic movement of the bones.

* * * * *